United States Patent
Eggenweiler et al.

(10) Patent No.: US 6,613,778 B1
(45) Date of Patent: Sep. 2, 2003

(54) IMIDAZOPYRIDINE DERIVATIVES AS PHOSPHODIESTERASE VII INHIBITORS

(75) Inventors: Hanse-Michael Eggenweiler, Weiterstadt (DE); Karl-August Ackermann, Weiterstadt (DE); Rochust Jonas, Darmstadt (DE); Michael Wolf, Darmstadt (DE); Michael Gassen, Griesheim (DE); Thomas Welge, Alsbach (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 0 days.

(21) Appl. No.: 10/129,274
(22) PCT Filed: Oct. 25, 2000
(86) PCT No.: PCT/EP00/10525
§ 371 (c)(1), (2), (4) Date: May 3, 2002
(87) PCT Pub. No.: WO01/34601
PCT Pub. Date: May 17, 2001

(51) Int. Cl.$^7$ .......................... A01N 43/42; A61K 31/44
(52) U.S. Cl. ...................................... 514/303
(58) Field of Search ............................ 546/118; 514/303

(56) References Cited

U.S. PATENT DOCUMENTS 4,654,350 A  * 3/1987 Irmscher et al. ............ 546/118

FOREIGN PATENT DOCUMENTS

EP  0 426 467 A  5/1991

OTHER PUBLICATIONS

M. Semonsky et al., "Substanzen mit antineoplasischer Wirkung" Arzneimittel Forschung. Drug Research., Bd. 20, Nr. 3, pp. 316–323, XP002170611, Editio Cantor. Aulendorf., DE ISSN: 0004–4172 Tabellen 1–3.

* cited by examiner

Primary Examiner—Alan L. Rotman
Assistant Examiner—Raymond Covington
(74) Attorney, Agent, or Firm—Millen, White, Zelano & Branigan, P.C.

(57) ABSTRACT

Compounds of the formula I

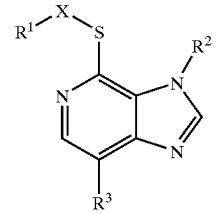

in which
- $R^1$ denotes $CONR^4R^5$,
- $R^2$ denotes H or A,
- $R^4$ and $R^5$, independently of one another, each denote H or $A^1$,
- $R^3$ denotes Hal,
- Hal denotes F, Cl, Br or I,
- A denotes alkyl having 1–4 carbon atoms,
- $A^1$ denotes alkyl having 1–10 carbon atoms,
- X denotes alkylene having 1–4 carbon atoms, in which an ethylene group may also be replaced by a double or triple bond, and their physiologically acceptable salts and/or solvates, as phosphodiesterase VII inhibitors, and their use for the preparation of a medicament.

12 Claims, No Drawings

IMIDAZOPYRIDINE DERIVATIVES AS PHOSPHODIESTERASE VII INHIBITORS

The invention relates to compounds of the formula I

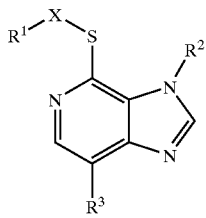

in which
- $R^1$ denotes $CONR^4R^5$,
- $R^2$ denotes H or A,
- $R^4$ and $R^5$, independently of one another, each denote H or $A^1$,
- $R^3$ denotes Hal,
- Hal denotes F, Cl, Br or I,
- A denotes alkyl having 1–4 carbon atoms,
- $A^1$ denotes alkyl having 1–10 carbon atoms,
- X denotes alkylene having 1–4 carbon atoms, in which an ethylene group may also be replaced by a double or triple bond, and their physiologically acceptable salts and/or solvates.

Other imidazopyridine derivatives having GABA-agonistic actions are disclosed, for example, in EP 82369.

The invention had the object of finding novel compounds having valuable properties, in particular those which can be used for the production of medicaments.

It has been found that the compounds of the formula I and their salts have very valuable pharmacological properties and are well tolerated.

In particular, they exhibit specific inhibition of "Rolipram insensitive" cAMP phosphodiesterase (PDE VII).

The biological activity of the compounds of the formula I can be determined by methods as described, for example, by M. A. Giembycz et al. in Br. J. Pharmacol. (1996), 118, 1945–1958.

The affinity of the compounds for cAMP phosphodiesterase (PDE VII) is determined by measuring their $IC_{50}$ values (concentration of the inhibitor that is required to achieve 50% inhibition of the enzyme activity). In order to carry out the determinations, homogenized SK-N-SH neuroblastoma cells were used instead of T-lymphocytes, and PDE III inhibition was carried out using Cl-930. This is a selective PDE III inhibitor (J. A. Bristol et al., J. Med. Chem. 1984, 27(9), 1099–1101). Alternatively, SK-N-SH is replaced by HUT-78 and instead of using Cl-930 inhibition is carried out with trequensin (D. Ruppert et al., Life Sci. 31:2037, 1982).

The compounds of the formula I can be employed for the treatment of asthmatic illnesses.

The anti-asthmatic action can be determined, for example, analogously to the method of T. Olsson, Acta allergologica 26, 438–447 (1971).

Since cAMP inhibits osteoclastic cells and stimulates osteogenetic cells (S. Kasugai et al., M 681, and K. Miyamoto, M 682, in Abstracts of the American Society for Bone and Mineral Research, 18th Annual Meeting, 1996), the compounds of the formula I can be employed for the treatment of osteoporosis.

The compounds also exhibit an antagonistic action to the production of TNFα (tumour necrosis factor) and are therefore suitable for the treatment of allergic and inflammatory diseases, autoimmune diseases, such as, for example, rheumatoid arthritis, multiple sclerosis, Crohn's disease, diabetes mellitus or ulcerative colitis, transplant rejection reactions, cachexia and sepsis.

The anti-inflammatory action of the substances of the formula I and their effectiveness for the treatment of, for example, autoimmune diseases.such as multiple sclerosis or rheumatoid arthritis can be determined analogously to the methods of N. Sommer et al., Nature Medicine 1, 244–248 (1995), or L. Sekut et al., Clin. Exp. Immunol. 100, 126–132 (1995).

The compounds can be employed for the treatment of cachexia. The anti-cachectic action can be tested in TNF-dependent models of cachexia (P. Costelli et al., J. Clin. Invest. 95, 2367 ff. (1995); J. M. Argiles et al., Med. Res. Rev. 17, 477 ff. (1997)).

The PDE VII inhibitors can also inhibit the growth of tumour cells and are therefore suitable for tumour therapy (for PDE IV inhibitors, cf. D. Marko et al., Cell Biochem. Biophys. 28, 75 ff. (1998)).

They can furthermore be employed for the therapy of sepsis and for the treatment of memory disorders, atherosclerosis, atopical dermatitis and AIDS, furthermore for the treatment of T cell-dependent diseases (L. Li et al., Science, 1999, 283, 848–851).

The compounds of the formula I can be employed as medicament active ingredients in human and veterinary medicine. They can furthermore be employed as intermediates for the preparation of further medicament active ingredients. In particular, the compounds of the formula I can be employed as medicament active ingredients for PDE VII inhibition in human and veterinary medicine.

The invention furthermore relates to the use of the compounds of the formula I for the preparation of a medicament for combating allergic diseases, asthma, chronic bronchitis, atopical dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

A denotes alkyl having 1–4 carbon atoms and has 1, 2, 3 or 4 carbon atoms and preferably denotes methyl, ethyl or propyl, furthermore preferably isopropyl, butyl, isobutyl, sec-butyl or tert-butyl. 1–7 H atoms in the radicals may also be replaced by F and/or Cl. A therefore also denotes, for example, trifluoromethyl or pentafluoroethyl.

$A^1$ denotes alkyl having 1–10 carbon atoms and has 1, 2, 3, 4, 5, 6, 7, 8, 9 or 10 carbon atoms and preferably denotes methyl, ethyl or propyl, furthermore preferably isopropyl, butyl, isobutyl, sec-butyl or tert-butyl, but also n-pentyl, neopentyl, isopentyl or hexyl. 1–7 H atoms in the radicals may also be replaced by F and/or Cl. $A^1$ therefore also denotes, for example, trifluoromethyl or pentafluoroethyl.

X denotes alkylene having 1–4 carbon atoms, preferably methylene, ethylene, propylene or butylene, in which one ethylene group may also be replaced by a double or triple bond. X therefore also denotes, for example, —$CH_2$— $CH=CH-H_2$— or —C≡—C—.

Accordingly, the invention relates, in particular, to those compounds of the formula I in which at least one of said radicals has one of the preferred meanings indicated above. Some preferred groups of compounds may be expressed by the following sub-formulae Ia to Ic, which correspond to the formula I and in which the radicals not designated in greater detail have the meaning indicated in the formula I, but in which

| | | |
|---|---|---|
| in Ia | R³ | denotes Cl; |
| in Ib | R³ | denotes Cl, |
| | X | denotes alkylene having 1–4 carbon atoms; |
| in Ic | R³ | denotes Cl, |
| | X | denotes alkylene having 1, 2, 3 or 4 carbon atoms, |
| | A¹ | denotes alkyl having 1, 2, 3 or 4 carbon atoms. |

The compounds of the formula I and also the starting materials for their preparation are prepared, in particular, analogously as described in EP 82369 on page 3, left-hand column, line 18, to page 4, column 6, line 16, or in Example 1.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for said reactions.

A base of the formula I can be converted into the associated acid-addition salt using an acid, for example by reaction of equivalent amounts of the base and the acid in a suitable solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethane-sulfonic acid, benzenesulfonic acid, p-toluenesulfonic acid, naphthalene-mono- and -disulfonic acids, laurylsulfuric acid. Salts with physiologically unacceptable acids, for example picrates, can be used for the isolation and/or purification of the compounds of the formula I.

The invention also relates to medicaments of the formula I and their physiologically acceptable salts as phosphodiesterase VII inhibitors.

The invention furthermore relates to pharmaceutical preparations comprising at least one phosphodiesterase VII inhibitor of the formula I and/or one of its physiologically acceptable salts and/or solvates for combating allergic diseases, asthma, chronic bronchitis, atopical dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

The substances here are generally preferably administered in doses of between about 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular disease to which the therapy applies. Oral administration is preferred.

The pharmaceutical preparations can be used as medicaments in human or veterinary medicine. Suitable excipients are organic or inorganic substances which are suitable for enteral (for example oral), parenteral or topical administration and with which the novel compounds do not react, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral administration are, in particular, tablets, pills, coated tablets, capsules, powders, granules, syrups, juices or drops, suitable for rectal administration are suppositories, suitable for parenteral administration are solutions, preferably oily or aqueous solutions, furthermore suspensions, emulsions or implants, and suitable for topical application are ointments, creams or powders. The novel compounds may also be lyophilized and the resultant lyophilizates used, for example, for the preparation of injection preparations. The preparations indicated may be sterilized and/or comprise auxiliaries, such as lubricants, preservatives, stabilizers and/or wetting agents, emulsifiers, salts for modifying the osmotic pressure, buffer substances, dyes, flavours and/or a plurality of further active ingredients, for example one or more vitamins.

The invention relates, in particular, to the compounds of the formula I listed in the examples below and their physiologically acceptable salts and/or solvates as PDE VII inhibitors and to their use for the preparation of a medicament for combating allergic diseases, asthma, chronic bronchitis, atopical dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

EXAMPLES 2-(3-Butyl-7-chloro-3H-imidazo[4,5-c]pyridin-4-ylsulfanyl)-N,N-dimethylacetamide

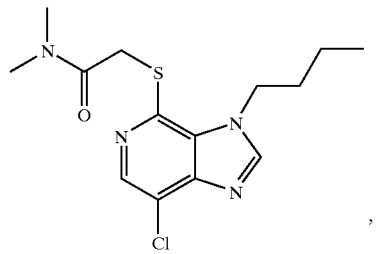

2-(3-butyl-7-chloro-3H-imidazo[4,5-c]pyridin-4-ylsulfanyl)acetamide, 2-(3-butyl-7-chloro-3H-imidazo[4,5-c]pyridin-4-ylsulfanyl)propionamide, 2-(3-butyl-7-chloro-3H-imidazo[4,5-c]pyridin-4-ylsulfanyl)butyramide, 2-(3-butyl-7-chloro-3H-imidazo[4,5-c]pyridin-4-ylsulfanyl)-N-hexylacetamide, 2-(3-butyl-7-chloro-3H-imidazo[4,5-c]pyridin-4-ylsulfanyl)-N-octylacetamide 4-(3-butyl-7-chloro-3H-imidazo[4,5-c]pyridin-4-ylsulfanyl)-but-2-enoic acid dimethylamide.

The examples below relate to pharmaceutical preparations:

Example A

Injection Vials

A solution of 100 g of a phosphodiesterase VII inhibitor of the formula I and 5 g of disodium hydrogenphosphate in 3 l of bidistilled water is adjusted to pH 6.5 using 2N hydrochloric acid, sterile filtered, transferred into injection vials, lyophilized under sterile conditions and sealed under sterile conditions. Each injection vial contains 5 mg of active ingredient.

Example B

Suppositories

A mixture of 20 g of a phosphodiesterase VII inhibitor of the formula I is melted with 100 g of soya lecithin and 1400 g of cocoa butter, poured into moulds and allowed to cool. Each suppository contains 20 mg of active ingredient.

Example C

Solution

A solution is prepared from 1 g of a phosphodiesterase VII inhibitor of the formula 1, 9.38 g of $NaH_2PO_4.2\,H_2O$, 28.48 g of $Na_2HPO_4.12\,H_2O$ and 0.1 g of benzalkonium chloride in 940 ml of bidistilled water. The pH is adjusted to 6.8, and the solution is made up to 1 l and sterilized by irradiation. This solution can be used in the form of eye drops.

Example D

Ointment 500 mg of a phosphodiesterase VII inhibitor of the formula I are mixed with 99.5 g of Vaseline under aseptic conditions.

Example E

Tablets

A mixture of 1 kg of phosphodiesterase VII inhibitor of the formula I, 4 kg of, lactose, 1.2 kg of potato starch, 0.2 kg of talc and 0.1 kg of magnesium stearate is pressed to give tablets in a conventional manner in such a way that each tablet contains 10 mg of active ingredient.

Example F

Coated Tablets

Tablets are pressed analogously to Example E and subsequently coated in a conventional manner with a coating of sucrose, potato starch, talc, tragacanth and dye.

Example G

Capsules 2 kg of phosphodiesterase VII inhibitor of the formula I are introduced into hard gelatine capsules in a conventional manner in such a way that each capsule contains 20 mg of the active ingredient.

Example H

Ampoules

A solution of 1 kg of phosphodiesterase VII inhibitor of the formula I in 60 l of bidistilled water is sterile filtered, transferred into ampoules, lyophilized under sterile conditions and sealed under sterile conditions. Each ampoule contains 10 mg of active ingredient.

Example I

Inhalation Spray 14 g of phosphodiesterase VII inhibitor of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

What is claimed is:

1. A compound of the formula I:

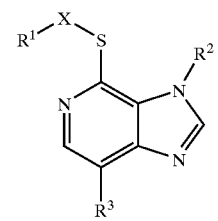

in which $R^1$ is $CONR^4R^5$, $R^2$ is H or A, $R^4$ and $R^5$, independently of one another, each is H or $A^1$, $R^3$ is Hal, Hal is F, Cl, Br or I, A is alkyl having 1–4 carbon atoms, optionally, wherein H atoms are replaced by F and/or Cl, $A^1$ is alkyl having 1–10 carbon atoms, optionally, wherein H atoms are replaced by F and/or Cl, X is alkylene having 1–4 carbon atoms, in which an ethylene group is optionally replaced by a double or triple bond, or a physiologically acceptable salt and/or solvate thereof.

2. A medicament composition comprising a compound of formula I according to claim 1, and at least one physiologically acceptable excipient or auxiliary.

3. A medicament composition according to claim 2, which exhibits the property of inhibiting phosphodiesterase VII.

4. A method for treating an allergic disease, asthma, chronic bronchitis, atopical dermatitis, psoriasis or another skin disease, an inflammatory disease, an autoimmune disease, osteoporosis, a transplant rejection reaction, cachexia, tumour growth or tumour metastases, sepsis, a memory disorder, atherosclerosis or AIDS, comprising administering to a patient in need thereof a medicament composition of claim 2.

5. A method of claim 4, which is for treating an autoinmune disease which is rheumatoid arthritis, multiple sclerosis, Crohn's disease, diabetes mellitus or ulcerative colitis.

6. A method of claim 4, wherein the method is for treating osteoporosis.

7. A compound of claim 1, wherein $R^3$ is Cl.

8. A compound of claim 1, wherein $R^3$ is Cl, and X is alkylene having 1–4 carbon atoms.

9. A compound of claim 1, wherein $R^3$ is Cl, X is alkylene having 1, 2, 3 or 4 carbon atoms, and $A^1$ is alkyl having 1, 2, 3 or 4 carbon atoms.

10. A medicament composition of claim 2, which is in dosage unit form wherein the compound of formula I is provided in a dose of between about 1 and 500 mg, per dosage unit.

11. A medicament composition of claim 2, which is in dosage unit form wherein the compound of formula I is provided in a dose of between 5 and 100 mg, per dosage unit.

12. A method of claim 4, wherein the compound of formula I is provided in a daily dose of between about 0.02 and 10 mg/kg of body weight.

* * * * *

UNITED STATES PATENT AND TRADEMARK OFFICE
CERTIFICATE OF CORRECTION

PATENT NO.     : 6,613,778 B1
DATED          : September 2, 2003
INVENTOR(S)    : Hans-Michael Eggenweiler It is certified that error appears in the above-identified patent and that said Letters Patent is hereby corrected as shown below:

Title page,
Item [75], Inventors, reads "Hanse-Michael" should read -- Hans-Michael --

Column 6,
Lines 58-59, reads "autoinmmune" should read -- autoimmune --

Signed and Sealed this

Fourteenth Day of September, 2004

JON W. DUDAS
*Director of the United States Patent and Trademark Office*